United States Patent [19]
Moser et al.

[11] Patent Number: 5,909,270
[45] Date of Patent: Jun. 1, 1999

[54] CONOSCOPIC SYSTEM FOR REAL-TIME CORNEAL TOPOGRAPHY

[75] Inventors: Christophe Moser; George Barbastathis; Demetri Psaltis, all of Pasadena, Calif.

[73] Assignee: California Institute of Technology, Pasadena, Calif.

[21] Appl. No.: 08/854,212

[22] Filed: May 9, 1997

Related U.S. Application Data

[60] Provisional application No. 60/017,539, May 10, 1996, and provisional application No. 60/028,945, Oct. 18, 1996.

[51] Int. Cl.⁶ .................................................. A61B 3/00
[52] U.S. Cl. ................................................... 351/212
[58] Field of Search .................................. 351/208, 211, 351/212; 606/4, 5, 12, 10, 11

[56] References Cited

U.S. PATENT DOCUMENTS

| | | |
|---|---|---|
| 5,395,356 | 3/1995 | King et al. . |
| 5,549,599 | 8/1996 | Sumiya . |
| 5,571,107 | 11/1996 | Shaibani et al. ............................ 606/4 |
| 5,603,709 | 2/1997 | Johnson .................................... 606/5 |
| 5,613,965 | 3/1997 | Muller . |
| 5,820,627 | 10/1998 | Rosen et al. ............................. 606/12 |

OTHER PUBLICATIONS

Gabriel Sirat and Demetri Psaltis, "Conoscopic Holography", Optic Letters/vol. 10, No. 1/Jan. 1985.

Gabriel Sirat, Conoscopic Holography: I. Basic Principles and Physical Basis, Journal of Optics Society/vo. 9, No. 1/Jan. 1992.

Gabriel Sirat, Conoscopic Holography. II. Rigorous Derivation, J. Opt. Soc. Am./vol. 9, No. 1/Jan. 1992.

Stanley Diamond, M.D., "Excimer Laser Photorefractive Keratectomy (PRK) for Myopia—Present Status: Aerospace Considerations", Aviation, Space, and Environmetnal Medicine, vo. 66, No. 7/Jul. 1995.

*Primary Examiner*—George Manuel
*Attorney, Agent, or Firm*—Fish & Richardson P.C.

[57] ABSTRACT

A corneal topographer based on conoscopic holography with partially coherent illumination. Corneal topographic measurements can be accomplished at a processing rate higher than the standard video rate of 30 Hz. The conoscopic measurements can be used in an opto-electronic servo to control a photorefractive keratectomy system in real time for an improved accuracy in laser ablation of a corneal surface.

16 Claims, 6 Drawing Sheets

CONOSCOPIC SYSTEM FOR REAL-TIME CORNEAL TOPOGRAPHY

CROSS-REFERENCE TO RELATED APPLICATIONS

This application claims the benefits of the U.S. Provisional Application No. 60/017,539, filed on May 10, 1996, and the U.S. Provisional Application No. 60/028,945, filed on Oct. 18, 1996. The disclosure of the above two provisional applications is incorporated herewith by reference.

FIELD OF THE INVENTION

The invention relates to surface topography using optical techniques, and more specifically, to a surgical system for obtaining topographical maps of a cornea based on optic conoscopic holography.

BACKGROUND OF THE INVENTION

Light entering the eye passes through several refractive elements including the cornea, the aqueous, the lens, and the vitreous before forming an image on the retina. Several vision problems are caused by the formation of defocused images on the retina due to eyeball or corneal deformations. Some common vision problems include myopia, presbyopia, hyperopia, and astigmatism. Refractive corneal surgery has been proven to be effective in compensating for these vision problems by reshaping the cornea, the most accessible refractive element of the eye, in a way so that the image focuses correctly on the retina.

Corneal shape correction can be achieved with an invasive surgical procedure such as radial keratectomy, Keratomileusis, and Kerato-phakia. A non-invasive procedure such as Photorefractive Keratectomy ("PRK") can also be used in which the corneal surface is ablated step-by-step with ultraviolet (UV) high-power laser pulses to achieve a desired shape. Another non-invasive procedure is Laser Photo Thermal Keratoplasty ("LPTK") in which the cornea is shaped by thermal effects resulting from irradiation of a laser beam.

The corneal shape determines the corrected vision acuity. The correction in the corneal curvature is conventionally measured in diopters, like many other quasi-spherical optical surfaces. Diopters are defined as a reciprocal of the focal length measured in meters. It is known that a deviation by 1 diopter from the desired correction can result in a visual acuity as low as 20/40. Therefore, accurate measurements of the corneal shape during the surgical procedure in order to minimize the surgical errors becomes critical.

PRK methods irradiate the patient's eye by a pulsed laser emitting at a wavelength in an ultra-violet (UV) spectral region in which the corneal tissue is highly absorptive. The corneal tissue is ablated by the high-energy laser pulses and the ablation depth produced by a laser pulse depends on the energy density or "fluence" of the laser pulse. On average in a typical PRK operation, a tissue depth of approximately 0.2~0.4 $\mu$m can be ablated per pulse with a laser fluence ranging from about 100 mJ/cm$^2$ to about 300 mJ/cm$^2$.

Two types of PRK procedures are commonly used, one using a uniformly expanded laser beam and another one using a focused scanning beam. The PRK technique based on a uniform beam expand the UV laser beam to approximately the size of the entire cornea. Accurate diameter control may be achieved by using an iris (i.e., a diaphragm). This method can be used in a treatment for the myopia, hyperopia or presbyopia, but not for astigmatism. The scanning beam PRK method focuses the laser beam to a small spot diameter on the cornea (e.g., approximately 1 mm). This small spot diameter is mechanically steered to access different locations on the cornea sequentially. The scanning beam method usually can be used to achieve a desired shaping profile with a better accuracy than that of the uniform beam method.

In many prior-art PRK procedures, a corrective operation is usually done in four steps. First, a desired topographic shape of the cornea of an eye is determined based on the specific vision problems in the eye. Secondly, the operating parameters, such as the total desired ablation depth and thereby the required number of pulses, are determined prior to the operation for the desired cornea shape. For a scanning PRK, a desired trace of the scanning beam also needs to be determined. Thirdly, the predetermined parameters are used to control the laser to perform the corrective procedure by reshaping the cornea. Lastly, the resultant topographical shape of the cornea is measured.

The above prior-art approach requires that all predetermined operating parameters remain constant during operation. For example, the laser fluence must be precisely known and remain constant during the entire operation. The topographic measurement is performed after the operation and only then can the success of the operation be evaluated.

However, a number of practical factors may adversely affect the above approach. For example, the corneal tissue may not be even and the absorption coefficient of a cornea can often have local variations. This may cause variations in the ablation depth at different locations on the cornea for a laser beam of a constant fluence. Thus, the final topographic shape of the cornea may deviate from a desired shape and the resultant vision can be significantly degraded.

The output power of a laser may also vary or fluctuate during an operation. This power drift in the laser beam can be caused by many factors, including temperature variations, mechanical vibrations, noise in the laser electronic control circuits and so on. In many cases, these factors are not easily controllable although various control servo techniques may be used to reduce the variations. The power variation of the laser can cause undesirable variations in the laser fluence. Consequently, the ablation depth of a pulse changes.

Furthermore, the alignment of the beam scanning system is known to change as well due to variations in the relative positioning of the laser and the beam scanning system, variations in the beam scanning system, and beam drift of the laser. This can cause the scanning laser beam to walk off from a prespecified scanning trace in a scanning PRK process, thereby resulting in an error in the final shape of the cornea. Any accidental movement of the eye during the operation could also adversely affect the operation.

Errors in the final corneal shape due to the above and other factors significantly reduce the effectiveness of the PRK procedures. A study of patients who were treated with a conventional PRK at the Doheny Eye Institute of the University of Southern California showed that about 95% of the patients achieved a corrected vision acuity 20/40 or better after the surgery (corresponding to a refractive error of less than 1 diopter) and only about 50% of these patients had a corrected vision acuity of 20/20 or better. The current relatively low success probability of PRK at least in part contributes to the existing doubt of the public on the PRK procedures despite many benefits and advantages of the PRK over the use of the corrective eye glasses or invasive surgical procedures. Many practitioners in the ophthalmology community believe that a success probability above 95% in achieving a corrected visual acuity of 20/20 with PRK may be necessary in convincing more people with visual problems to receive the beneficial PRK treatment.

In recognition of the above, it is desirable to have precise active control of the ablation progress in real time in order to compensate for the above variations during a PRK operation. This requires acquisition of corneal topographic data of the 3-dimensional shape of the corneal surface within the time interval between two successive ablating pulses. In this context, the topographic measurements are performed in "real time". The topographic data is then fed back to the diaphragm/beam-steering control system to adjust the operating parameters. This active feedback control mechanism can be used to minimize the deviation of the final corneal shape from the ideal shape during the operation.

In order to ascertain the results of the operation, resolution of 0.1 diopters in the corneal curvature measurement would be desirable. The amount of diopter correction as function of ablation depth at the center of the cornea can be calculated geometrically.

The result for the case of myopia is shown in FIG. 1. The curve in FIG. 1 shows that 0.1 diopters correspond to an ablation depth of about 1.3 $\mu$m which can be achieved with roughly 4–7 laser pulses in a typical PRK system. At a pulse repetition rate of 50 Hz, this requires one complete topographical measurement every 80 msec or faster. In a transverse direction along a corneal surface, the resolution is mainly determined by the pixel size of the camera and the apertures of the optics used in the optical system. A typical camera can provide a resolution of about 250,000 pixels. If the entire corneal surface, typically about 29 mm$^2$ in area, is imaged on the camera, an effective spatial resolution of approximately 10 $\mu$m is obtained. Commercial systems typically have a resolution on the order of a few hundred microns. Assuming an acceptable lateral resolution at 100 $\mu$m in the beam diameter spot, about 2,500 of pixels need to be processed.

The measured topographic data can be used both for graphical display and feedback to the beam-steering controls of the system. To account for delays in the calculation of the required mirror positions and the mechanical response, a faster operation of the measurement system may be reasonably assumed. One estimate for the data processing rate is 30 ms or 30 Hz, which corresponds to the standard video rate. This leads to approximately 83,000 pixels per second.

However, the conventional corneal topographic systems are limited in providing the above real-time topographic measurements during the surgery. One commercial corneal topography system, for example, projects calibrated fringe patterns on the cornea, captures the reflection using a CCD camera, and then digitally processes the distortions on the fringe pattern in order to deduce the deviation of corneal surface from a perfect sphere. The amount of calculation required to perform this operation cannot be performed at a speed of 83,000 pixels/sec that is desirable for a real-time.

In addition, the conventional corneal topographic systems impose various other constraints that make them unsuitable for real-time surgical monitoring.

For example, several commercial topographic systems project Placido rings on a corneal surface and capture the specular reflected pattern from the cornea with a camera. The captured pattern is then digitized and measured to determine the fringe distortion. Thus, an one-to-one mapping between the surface deformation and the fringe shape is established. One limitation of this approach is the long processing time, usually on the order of 10 seconds or 0.1 Hz in terms of the processing rate. This is too slow for a real-time corneal topographic measurement required for a PRK treatment. Another limitation is that the Placido ring technique may work well on smooth specularly reflective surfaces but the performance is severely degraded for a scattering or diffusive surface. In a PRK surgery, the epithelium on a corneal surface is removed so that the surface is no longer perfectly specular but has a degree of scattering due to the laser ablation. This can undermine the effectiveness of the Placido ring method in a real-time corneal topography during a PRK operation. In addition, the Placido ring method requires the imaging camera to be placed at certain right angles to capture the fringes. This may limit the access of the ablating laser beam to the cornea.

A triangulation technique is also used as a conventional topographic method. A computer controls the pitch of the projected fringes on the corneal surface and acquires the images from the camera. The captured images are processed to obtain the fringe edge distortion data which constructs an isoheight map of the corneal surface. In a binocular configuration, the position of a point of interest on a corneal surface is extracted in three-dimensional space by intersecting the lines connecting the point to two cameras.

One limitation in the binocular-triangulation-based technique is the need to have a reference point on the cornea for a 3D mapping. This is difficult to obtain for a corneal surface which lacks pronounced features (e.g. a shape with edges and texture). Another limitation is the requirement to obtain a nearly perfect calibration, since a slight error in the knowledge about the relative location of the two cameras can induce large errors in the inferred surface shape.

Alternatively, a monocular configuration may be used for a triangulation system. Only a single camera is needed. A light projector can effectively serve as a second, active camera to replace a second passive camera in the above binocular configuration. A reference point is no longer necessary in the monocular technique. The light projector is used to project fringe or grid patterns of varying spatial frequency on the cornea. The topographic information is obtained by observing the deformations in the fringe edges.

Commercial corneal topographers based on triangulation can be used for a scattering corneal surface and allow access to a corneal surface by a ablating laser beam. Since the camera images a scattering surface at an angle, only a small portion of the reflected light from the surface may be captured. Therefore, it is often necessary to deposit a reflectivity enhancing material such as sodium fluorescein on the cornea in order to improve its reflectivity. The processing speed is usually slow, typically on an order of 5 to 10 seconds for a full corneal shape on which about 1000 points are sampled. In addition, the imaging resolution is about 0.2 mm.

Coherent holographic interference has also been used in some commercial topographers. Some aspects of this approach can be found, for example, in Am. J. Optometry & Phys. Optics, Vol. 65(8), pp. 653–660 (1988) by Smolek and in J. Cataract Refract. Surg., Vol.19S, pp. 182–187 (1993) by Burris et al. One limitation of this technique is the inherent speckle noise in a coherent holographic system. The inventors of the present invention evaluated this method for corneal shape measurements on swine eyes by both calculations and experiments. It was found that strong speckle noise was present in the captured images by illuminating the surface of a swine eye without the epithelium with a laser beam. The speckle noise makes it very difficult to form a topographic measurement. Well-known speckle reduction techniques, such as those disclosed by Iwai and Asakura in "Speckle reduction in coherent information processing", IEEE proceedings, Vol. 84(5), pp. 765–781 (1996), are usually cumbersome to incorporate in a commercial system, and cannot completely eliminate the speckle noise since they are incompatible with holographic recording.

The holographic techniques also suffer from power and stability limitations. The allowable power that may be applied on an eye without causing damage is within a range approximately from about 300 $\mu$W to about 400 $\mu$W. A reflected light beam with about 6–8 $\mu$W is usually available for recording a hologram for a typical eye with a reflectivity of about 2%. Conventional photopolymers are reasonably sensitive media in the red region of the spectrum. The time required to accumulate enough energy to record a hologram in such material would be on the order of a few hundred milliseconds, during which the patient's eye and the optical system must be completely stabilized. This is difficult in practice because of periodic eye movements and other instabilities that may occur under surgery room conditions.

SUMMARY OF THE INVENTION

In view of the above, the inventors recognized that conventional corneal topographers are usually not suitable for monitoring a corneal surface in real time during a PRK process. The conventional systems are limited by a number of factors including processing speed, noise and geometrical restrictions.

The present invention as fully disclosed in this disclosure overcomes these limitations, at least in part, by implementing a real-time topographer based on conoscopic holography. According to an embodiment of the invention, a partially coherent light source is preferably used to produce a probe beam for illuminating a target corneal surface of an eye at a fixed position. A collimating optical element such as a lens collimates the probe beam which is guided to the target cornea at an angular incidence. A collecting lens is placed relative to the target cornea along an optical path of the conoscopic topographer to receive and collimate a reflected probe wave from the target cornea. A birefringent crystal is positioned at a predetermined orientation relative to the collecting lens decomposes the reflected probe wave into ordinary waves and extraordinary waves. Two mutually-orthogonal polarizers are placed in the optical path with one on each side of the crystal. An imager such as a CCD camera is used to capture the conoscopic pattern caused by the interference between the ordinary and extraordinary waves. A frame grabber may be used to digitize the interference pattern. A system controller having a microprocessor is used to extract the three-dimensional topographic information of the reflecting corneal surface.

One aspect of the present invention is the use of conoscopic holography to capture the topographic information of a corneal surface. One advantage of this approach is a high resolution which is on an order of one wavelength. Another advantage is a single-step detection of deformation in the corneal surface. Yet another advantage is the use of partially coherent or incoherent light sources to minimize the speckle noise caused by a specular reflection from the cornea.

Another aspect of the invention is a hybrid opto-electronic system for the extraction of a corneal shape. The corneal shape is optically imprinted on the wavefront of the reflected probe beam and is recorded in conoscopic interference fringes. The corneal shape is then extracted by capturing the optical conoscopic interference pattern with an imager and processing the topographic information with a microprocessor. According to one embodiment, the microprocessor is programmed to perform a corneal shape extraction from the sheared interferogram based on a technique using Hermite polynomial expansions. This aspect of the invention allows a high speed operation and provides a real-time measurement in PRK operations.

Yet another aspect is a measurement of the deviation of a corneal surface from a desired model shape based on the conoscopic interference pattern. A conoscopic topographer in accordance with the invention can be implemented in a PRK system to improve the performance of PRK operations with high accuracy and minimal human intervention. In particular, the corneal surface can be measured in real time between ablating laser pulses to monitor ablation result of each pulse. The measurements can be fed back in a servo control to adjust the driving mechanism of the ablating laser and the beam control system, thus allowing a accurate control of the ablation profile.

BRIEF DESCRIPTION OF THE DRAWINGS

These and other aspects and advantages of the present invention will become more apparent in light of the following detailed description of preferred embodiments thereof, as illustrated in the accompanying drawing, in which.

DETAILED DESCRIPTION OF THE PREFERRED EMBODIMENT

Figure 1:
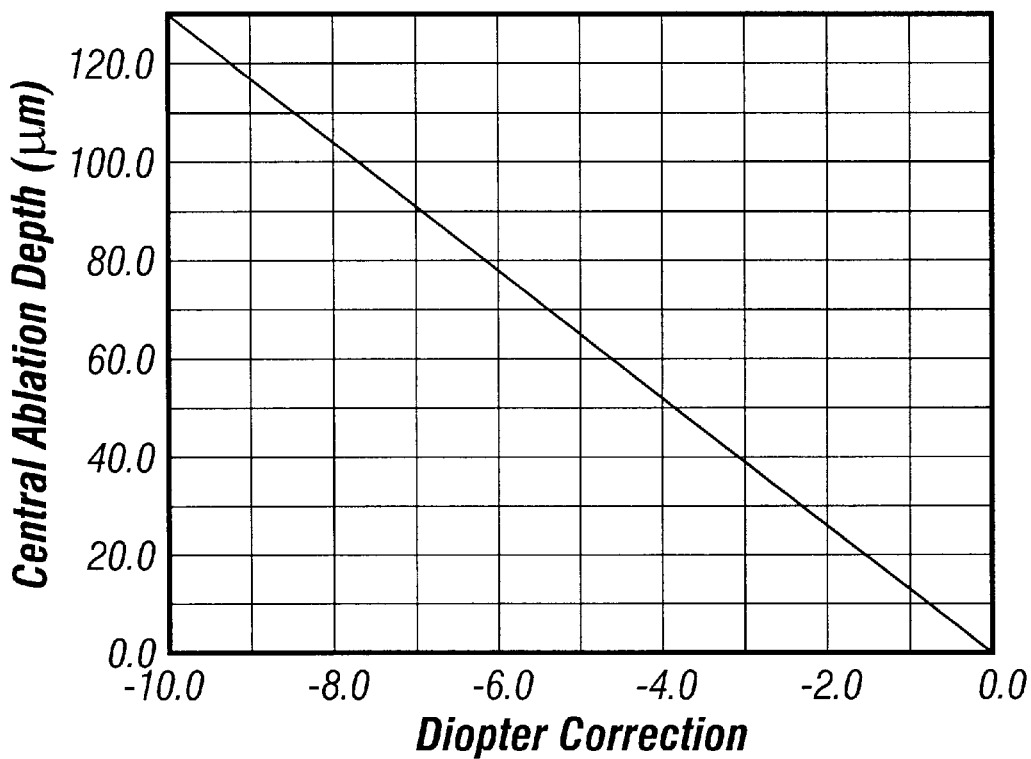
FIG. 1 is a chart showing ablation depth at the center of the cornea as a function of achieved diopter correction for myopia.
Figure 2:
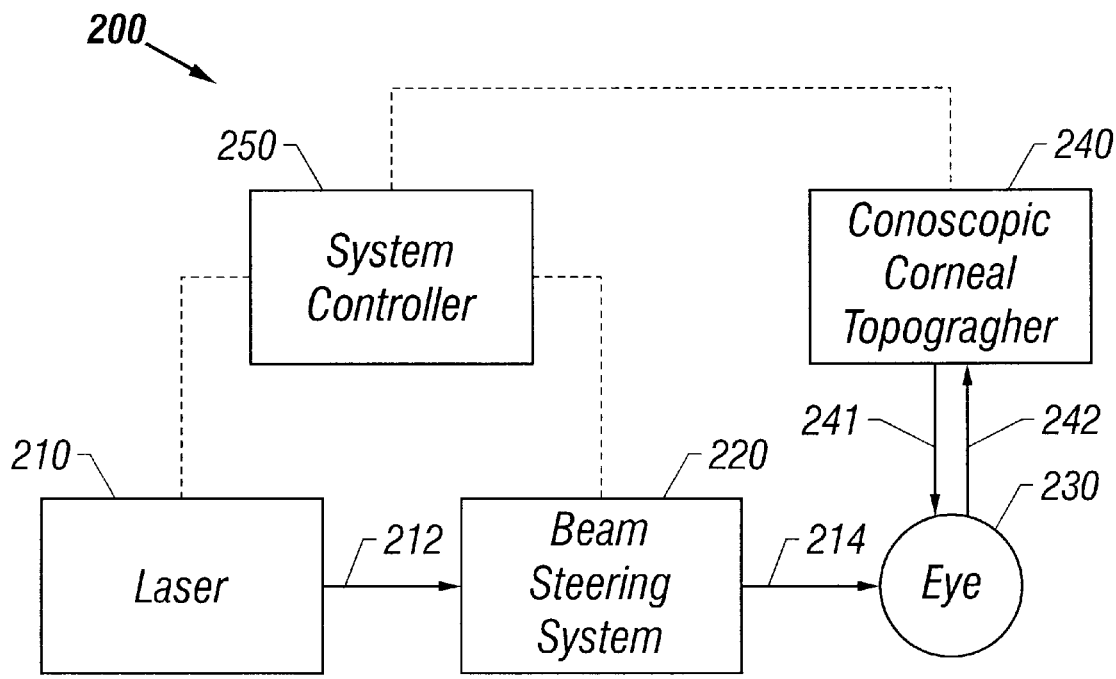
FIG. 2 is a block diagram of a preferred embodiment of a PRK system with a conoscopic topographer.

FIG. 2 is a block diagram showing one embodiment 200 of the PRK surgical system with a conoscopic corneal topographer 240 of the invention. The dashed lines indicate electrical signals and the arrowed lines indicated optical signals. A laser 210 is preferably a UV laser operating in a spectral range in which the corneal tissue is absorptive. Excimer lasers emitting at wavelengths from about 150 nm to 250 nm are widely used for PRK. Other lasers may also be used, such as UV solid-state lasers and diode-pumped lasers. A beam 212 produced by the laser 210 is guided to a target eye 230 as a beam 214 by a beam steering system 220. The laser 210 preferably produces a pulsed laser output. The pulse repetition rate and the pulse duration of the laser 210 may be adjusted.

The beam steering system 220 may have at least one mirror mounted on a galvanometer or other motion control device. The beam steering system 220 may have beam focusing optics for performing a scanning beam PRK operation or a beam expander for performing a uniform beam PRK operation. Therefore, the beam 212 and the beam 214 may have different beam properties, for example, different beam diameters and divergence.

A system controller 250 may include a microcontroller or a microprocessor for controlling the operations of the PRK system 200. For example, the output energy or power of the laser 210 may be controlled at any time by the system controller 250 to change the laser fluence at the surgical spot on the eye 230. Alternatively, the laser output may be changed by an electrically-controlled beam attenuator deployed in the path of the laser beam. The system controller 250 also controls the operation of the beam steering system 220 to guide beam 214 to a desired location on the target eye 230. A user may program the system controller 250 so that the focused beam 214 is scanned on the corneal surface of the eye 230 over a predetermined trace pattern in a scanning beam PRK operation.

A conoscopic corneal topographer 240 in the PRK system 200 is a corneal topographer based on the conoscopic holographic technique. A probe beam 241 is generated by an independent light source in the topographer 240. The probe beam 241 illuminates the cornea to produce a reflected probe beam 242 which is indicative of the phase variations of the cornea surface. A birefringent optical medium is deployed in the topographer 240 to generate a conoscopic interference pattern by the interference between an ordinary wave and an extraordinary wave of the reflected beam 242. The interference pattern represents the phase information of the corneal surface which is indicative of the topographical shape of the cornea. The interference pattern is then processed by the system controller 250 to extract the topographic shape of the cornea. The topographic shape of the cornea obtained from the topographer 240 provides an accurate measurement of the corneal surface ablated by the ablating laser beam 214.

The topographer 240 in accordance with an embodiment of the invention can process the corneal topographic information during the PRK operation at a processing rate higher than the pulse repetition rate of the laser 210. Thus, the topographic measurement can be used to monitor the results from each pulse of the ablating laser beam 214. This allows detection of the desired ablation depth at a desired location on a pulse by pulse basis.

An ideal topographic shape of the cornea of a patient's eye is predetermined based on a diagnosis of the patient's eye condition and the desired corrected vision that is to be achieved by the PRK treatment. The topographic information of the ideal cornea shape is stored in a memory unit of the system controller 250.

According to the present invention, the real-time topographic measurements can be used to control the laser 210 or the beam steering system 220. Any deviation from the predetermined ideal topographic shape may be corrected in real time during the PRK operation. As described above, the laser fluence may vary or fluctuate and the ablating beam position on the cornea may "walk off" from the desired beam trace. In addition, the surface properties of a cornea may not be uniform across the entire corneal surface. In particular, the absorption coefficient of the cornea may have local variations. These and other factors can adversely affect the outcome of a PRK operation. By dynamically adjusting the ablating laser beam position and the laser fluence based on the ablation depth and ablated location of a precedent laser pulse, the system 200 can significantly improve the performance of the PRK operation over the conventional systems.

For example, the system controller 250 may command the beam steering system 220 to adjust the beam positioning on the corneal surface of the ablating beam 214 based on the topographic measurement directly after a preceding pulse. This may show that the preceding pulse is deviated from a desired ablating trace. If topographic measurement right after a preceding pulse indicates that the ablation depth produced by a preceding laser pulse has deviated from the ideal depth due to a variation in the laser fluence or in the absorption coefficient of the cornea in that region, the system controller 250 may control the laser 210 to adjust the laser fluence of a subsequent laser pulse to a corrected value.

A preferred embodiment for the conoscopic corneal topographer 240 is based on the concept of conoscopic holography. See, for example, Sirat and Psaltis in "Conoscopic Holography", Optics Letters, Vol. 10(1), pp. 4–6 (1985), Sirat in "Conoscopic Holography. I. Basic principles and physical basis", Journal of Optical Society of America, Vol. A9(1), pp. 70–83 (1992) and "Conoscopic Holography. II. Rigorous derivation", Journal of Optical Society of America, Vol. A9(1), pp. 84–90 (1992). Conoscopic holography is a method for forming interference fringes with quasi-monochromatic but not necessarily coherent light sources. It is implemented with a highly birefringent optical medium, for example, a calcite crystal. The birefringent crystal is illuminated by a linearly-polarized light from a light source. Each ray entering the crystal is refracted into two types of rays, an ordinary ray ("o-ray") and an extraordinary ray ("e-ray"). These two types of rays experience different phase delays because of their different indices of refraction in the crystal, unless both rays propagate along a crystal optic axis. An interference pattern can be obtained by the interference between the two different rays.

Figure 3:
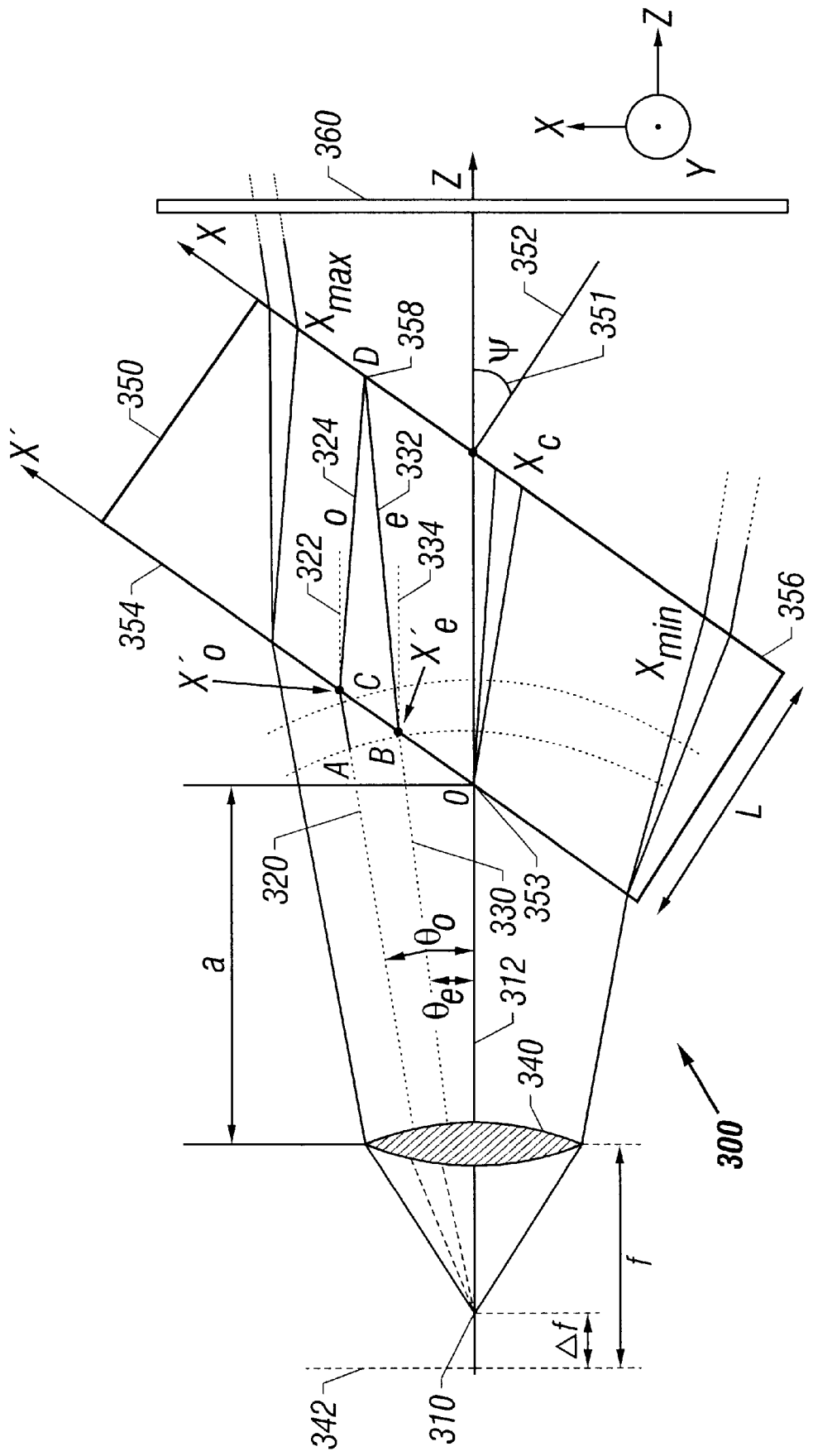
FIG. 3 is a schematic illustration of a tilted crystal geometry for conoscopic holography.

FIG. 3 shows a special conoscopic holography configuration 300 with a tilted uniaxial birefringent crystal in accordance with the present invention. The system 300 includes a quasi-monochromatic point source 310, a lens 340, a birefringent crystal 350, and a polarizer 360 that are positioned relative to one another to form an optical train along a system optic axis 312. The point source 310, which can be coherent, partially coherent, or incoherent, is located at or close to the front focal plane 342 of the lens 340. The crystal 350 has a crystal optic axis 352 along which an o-ray and an e-ray undergo the same phase delay. The crystal 350 is disposed in an orientation to form a tilted angle 351 ($\Psi$) with the system optic axis 312. Two exemplary light rays 320 and 330 from the point source 310 are shown in FIG. 3 to illustrate the operation. The rays 320 and 330 divide into their own o-rays, 324 and 334, and e-rays, 322 and 324, respectively, since rays 320 and 330 do not propagate along the crystal optic axis 352 due to the tilting of the crystal.

Figure 4:
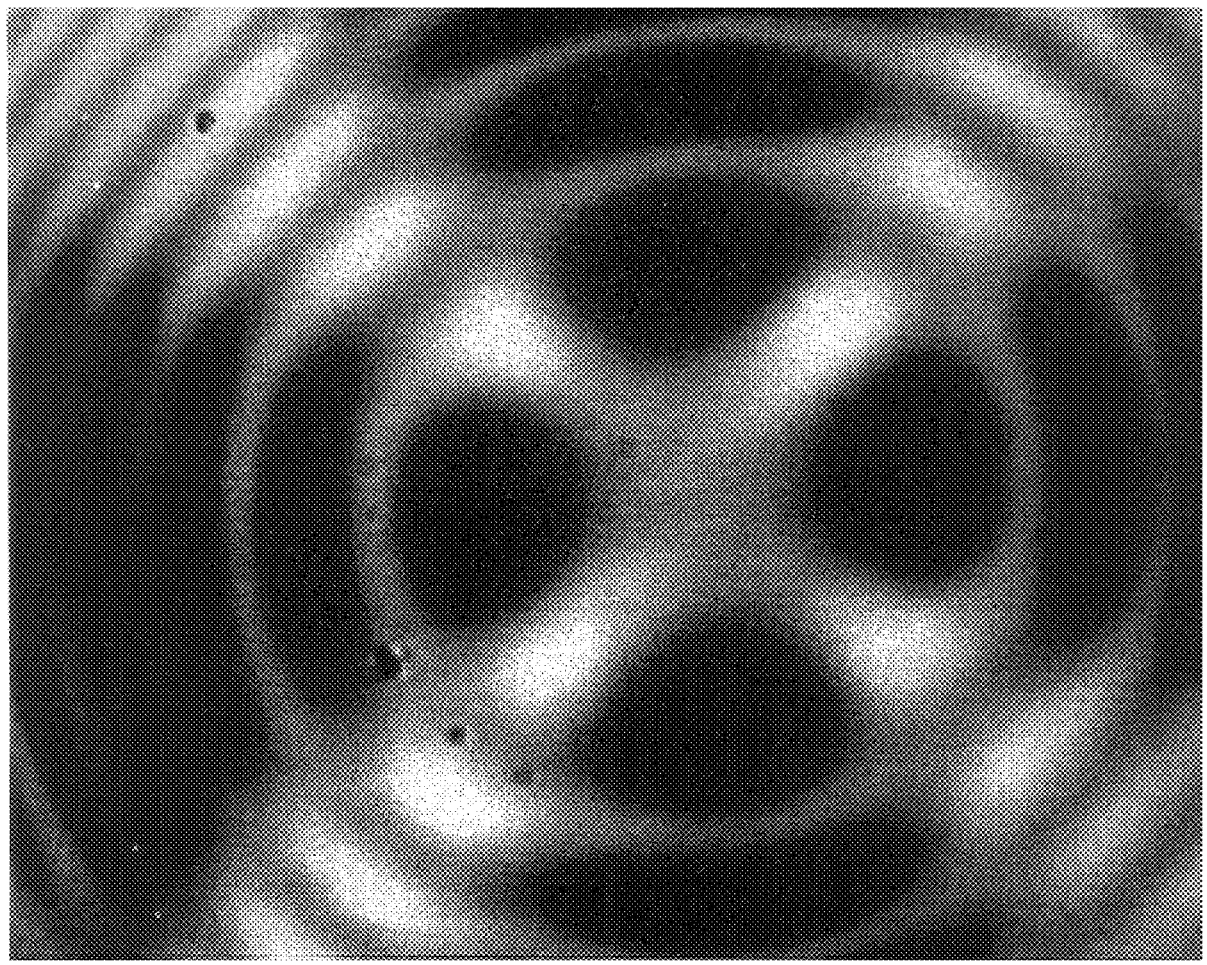
FIG. 4 is a photograph of a typical conoscopic pattern obtained with the system of FIG. 3.

The o-ray 324 coming from the ray 320 can combine with the e-ray 332 from the ray 330 at the exit surface 356 for a proper spatial separation of rays 320 and 330 on the entrance face 354 of the crystal 340. The two modes are mixed by using the polarizer 360 to form an interference pattern due to the difference in phase delay between the two interfering rays 324 and 332. The conoscopic interference pattern of a simple point source is similar to a Fresnel zone plate with a superimposed cross (bright or dark, depending on the analyzer orientation) parallel to the eigenaxes. The cross may be eliminated using circularly polarized light. FIG. 4 shows a typical conoscopic pattern obtained with a tilted calcite crystal in the system 300.

It is known that the interfering rays in a conoscopic setup typically sustain very small path difference and they originate at neighboring locations if an extended source is used. Therefore the temporal and spatial coherence requirements for a high-contrast interference pattern are much less stringent than the conventional coherent holographic interferometric techniques. As a result, only near-monochromaticity is required for the light source in a conoscopic setup. Thus, a variety of light sources may be used for conoscopic holography, including a light source that is both temporally and spatially coherent (e.g., a laser) and a highly incoherent quasi-monochromatic light source (e.g., a gas discharge lamp). The point source 310 is used here for simplification of the geometry.

The interference intensity pattern is a function of the total phase difference between the interfering beams from the point source 310 to the interfering point (e.g., 358) on the exit surface 356 of the crystal 350. Specifically, the fringe spacing is related to the defocus distance Δf between the point source 310 and the focal plane 342, the focal length f of the lens 340, the tilt angle 351 (Ψ), the thickness L, and the refractive properties of the uniaxial crystal 356.

Let G(x) be the total optical path difference and x be the radial distance from the system optic axis 312 to the interfering point 358. The optical intensity of the interference pattern after the polarizer 360 can be approximately expressed as:

$$I(x) = \frac{I_o}{2}\left[1 + \cos\left(\frac{2\pi G(x)}{\lambda}\right)\right] \quad (1)$$

where $I_o$ is an averaged light intensity in the interference field received by the imager. The optical path difference, G(x), can be calculated for the specific geometry of the conoscopic configuration. For the conoscopic system 300 using the uniaxial birefringent crystal 350 with indices of refraction for the ordinary and extraordinary rays as $n_o$ and $n_e$, G(x) can be shown to have the following form:

$$G(x) = n_0 L\left(\frac{n_e}{\sqrt{n_e^2 - \sin^2(\Psi - \theta_e(x))}} - \frac{n_o}{\sqrt{n_o^2 - \sin^2(\Psi_o(x))}}\right) + \quad (2)$$

$$L\left(\frac{n_o}{n_e}\frac{\sin(\Psi - \theta_e(x))}{\sqrt{n_e^2 - \sin^2(\Psi - \theta_e(x))}} - \frac{\sin^2(\Psi - \theta_o(x))}{\sqrt{n_o^2 - \sin^2(\Psi - \theta_o(x))}}\right) \times$$

$$\left\{\sin\Psi + \frac{\Delta f \cos^2\Psi}{2f(f + \Delta f)}\left[L\left(\frac{n_o}{n_e}\frac{\sin(\Psi - \theta_2(x))}{\sqrt{n_e^2 - \sin^2(\Psi - \theta_e(x))}} + \frac{\sin^2(\Psi - \theta_o(x))}{\sqrt{n_o^2 - \sin^2(\Psi - \theta_o(x))}}\right) - 2x\right]\right\},$$

where $\theta_o$ and $\theta_e$ are given by:

$$\theta_o(x) = \frac{\left(x - L\frac{\sin(\Psi - \theta_o(x))}{\sqrt{n_o^2 - \sin^2(\Psi - \theta_o(x))}}\right)\cos\Psi}{f\left(1 + \frac{f}{\Delta f}\right) - a - \left(x - L\frac{\sin(\Psi - \theta_o(x))}{\sqrt{n_o^2 - \sin^2(\Psi - \theta_o(x))}}\right)\sin\Psi}, \quad (3)$$

$$\theta_e(x) = \frac{\left(x - \frac{n_o}{n_e}L\frac{\sin(\Psi - \theta_e(x))}{\sqrt{n_e^2 - \sin^2(\Psi - \theta_e(x))}}\right)\cos\Psi}{f\left(1 + \frac{f}{\Delta f}\right) - a - \left(x - \frac{n_o}{n_e}L\frac{\sin(\Psi - \theta_e(x))}{\sqrt{n_e^2 - \sin^2(\Psi - \theta_e(x))}}\right)\sin\Psi}. \quad (4)$$

The distance a in Eqs. (3) and (4) is the distance from the lens 340 to the intercept point 353 of the system optic axis 312 and the entrance surface 354 of the crystal 350. A set of similar equations can be derived for the y-direction since the optic axis of crystal is in the xz-plane. The description of the y-direction will be neglected throughout the disclosure for simplicity.

Figure 5:
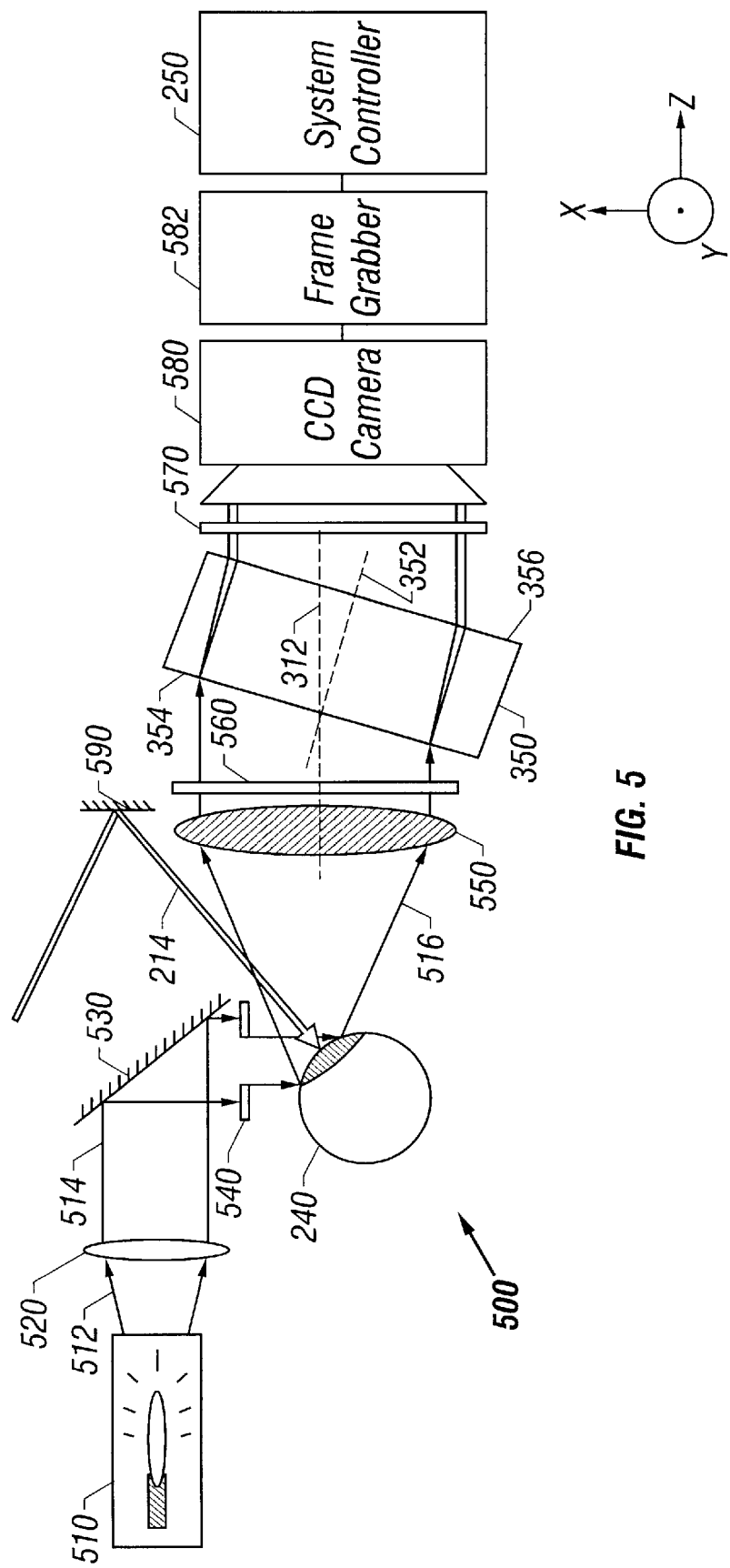
FIG. 5 is a schematic diagram of a special configuration of a conoscopic topographer in accordance with the invention.

FIG. 5 is a schematic illustration of a special implementation of the real-time conoscopic corneal topographer 240 of the PRK system 200 (FIG. 2) based on the conoscopic system 300 of FIG. 3. The conoscopic interference pattern is generated by a reflected probe beam off an eyeball.

A partially coherent light source 410 is preferably used to illuminate the eyeball 240 at a fixed position. Collimating optics 520 (e.g., a lens) collimates a light beam 512 produced by the light source 510. The collimated beam 514 is then directed to pass through an iris 540 to illuminate the eyeball 240. At least one mirror 530 may be optionally used to facilitate the guidance of the collimated beam 514. Preferably, the collimated beam 514 is incident to the eyeball 240 at an angle as illustrated in FIG. 5 because the ablating laser beam 214 produced by the laser 210 needs to impinge the eyeball 240 at a near normal incidence. The angular incident geometry of the probe beam allows easy access to the cornea by the ablating laser beam 240 and does not adversely affect the performance of the topographer.

A portion of the collimated beam 514 is reflected by the eyeball 240 as a reflected beam 516. Since the eyeball 240 has an approximately spherical shape, the reflected beam 516 diverges. A collecting lens 550 is placed relative to the eyeball 240 along the optical path of the conoscopic topographer approximately re-collimates the light beam 516 and directs the reflected beam to the birefringent crystal 350 that is sandwiched between two crossed polarizers, a polarizer 560 and an analyzer 570. An imager 580, such as a CCD camera, is positioned behind the polarizer 570 to capture the conoscopic interference pattern imprinted in the light beam emerging from the birefringent crystal 350. A frame grabber 582 may be used to digitize the interference pattern. The interference pattern is then fed to the system controller 250 and is processed to extract the information about the curvature and shape of the reflecting corneal surface.

An alignment laser (not shown) is often used to facilitate fixing the target eye 240. The alignment laser is usually a low-intensity red laser that produces a red beam in the direction of the ablated beam 214. A patient lies down on a table and is asked to look at the red beam. This aligns the red beam to be substantially perpendicular to the target eye 240. Therefore, the ablating beam 214 is also substantially perpendicular to the target eye 240.

One way to align the collecting lens 550 is by using the interference fringes after the analyzer 570. The collecting lens 550 may be mounted on a positioner to facilitate the alignment. A suitable positioner can be, for example, a translation stage or a piezo device for precise positioning control. The collecting lens 550 is adjusted to a position relative to the eye 240 at which the spacing of the observed conoscopic fringes is maximized.

The polarizer 560 is preferably placed between the eye 240 and the crystal 350. However, the polarizer 560 may be placed anywhere in the optical path of the probe beam prior to entering the crystal 350. According to the present invention, the reflected probe beam at the entrance surface of the crystal preferably has such a linear polarization with respect to the orientation of the crystal so that the ordinary and extraordinary waves have a substantially equal intensity relative to each other. This desired condition increases the contrast of the interference pattern.

For a Cartesian coordinate system in the special system 500 of FIG. 5, the polarizer 560 preferably has an angle of 45° with respect to either the positive x direction or the negative x direction.

The special system 500 is preferably calibrated by using a reflective spherical surface with known dimensions. A metallic calibration sphere may be used, for example. Since the exact shape of the calibration sphere is known, the optical aberration errors of the system 500 can be measured by the actual shape measurements with the calibration sphere. This calibration results are stored in the system controller 250 for calibrating measurements.

The inventors discovered that the coherence properties of the light source 510 can significantly affect the performance of the real-time conoscopic topographic measurements. The light source 510 should be selected based on the performance specifications of the system and the requirements of the conoscopic interferometry. The following factors are used in selecting a proper light source 510:

1. The spatial coherence of the light source 510 is necessary for achieving a good visibility or contrast of the conoscopic fringes. The visibility improves as the degree of spatial coherence of the light source 510 increases.
2. The noise performance of the conoscopic system deteriorates as the degree of temporal coherence of the light source 510 increases due to the speckle noise caused by the interference of rays reflected from neighboring points on a specular surface.
3. The wavelength and the power level of the light source 510 should be eye-safe. An eye-safe power level is considered at about 200 $\mu$W. The wavelength for the probe beam produced 510 may be from the visible spectrum to the IR range.
4. Since the reflectivity of the eye is typically about only 2%, the light source 510 should be sufficiently strong within the eye-safe power limit in order to achieve a sufficient signal intensity at the imager 580. The laser power delivered to the entire cornea is preferably at approximately 100 $\mu$W or more if a typical commercial CCD array is used as the imager 580. The laser power at the cornea may vary depending on the detection efficiency and sensitivity of the imager 580 used.

The inventors tested the special system 500 with various light sources based on the above guidelines. In testing the system 500, a uniaxial calcite crystal of 30 mm×30 mm×40 mm was used as the birefringent crystal 350, a CCD camera manufactured by the ImagePoint Corporation was used as the imager 580, and a Pentium personal computer was used as part of the system controller 250. The tests were performed with swine eyes in vitro. Test results with four types of light sources, lasers, current-swept laser diodes, sodium lamps, and VCSELs are summarized in Table 1.

TABLE 1

| Source | Advantages | Problems |
| --- | --- | --- |
| HeNe laser | high power high spatial coherence | strong speckle potential dangerous |
| Sodium lamp | no speckle | low power low fringe visibility (low spatial coherence) |
| Laser diode, current-swept | power & coherence | strong speckle (insufficient sweeping range) |
| VCSEL, small bandwidth (Linewidth < 7 × 10$^{-3}$nm) | power & coherence | strong speckle |
| Super Luminescent diode | no speckle | medium fringe visibility |

TABLE 1-continued

| Source | Advantages | Problems |
| --- | --- | --- |
| linewidth ~10 nm | sufficient power | (limited spatial coherence) |

The tests clearly show the trade-off between the coherence of the light source and the noise performance of the conoscopic topographer. Light sources with high spatial and temporal coherence such as a He—Ne laser and a vertical-cavity surface-emitting laser diode ("VCSEL") with a narrow bandwidth (e.g., less than 7×10$^{-3}$ nm) can produce fringes with high visibility in imaging optical quality surfaces. However, these highly coherent light sources produce strong speckle noise when used with highly specular surfaces such as the corneal surface. On the other hand, incoherent sources such as a sodium lamp can yield low power efficiency because of a wide angular emission distribution and poor fringe visibility. Since spatial coherence is necessary, a pin hole may be placed in front of an incoherent light source (e.g., sodium lamp) to increase the degree of the spatial coherence of the probe beam impinging on the cornea. The use of the pin hole significantly reduces the useful probe beam power. The speckle noise, however, is greatly reduced compared to the results of coherent light sources.

The best results were obtained using a super luminescent diode (e.g., Hamamatsu L3302) among the tested light sources listed in Table 1. The super luminescent diode operates at $\lambda$=850 nm with a bandwidth about 10 nm. This offers a balance between the coherence and speckle noise. A VCSEL made by Honeywell can also be used, which has a nominal bandwidth of about 0.5 nm near 850 nm. A degree of monochromaticity of the light source 510 can be characterized by a ratio of the emission linewidth $\Delta\lambda$ and the center wavelength $\lambda$. According to the invention, $\Delta\lambda/\lambda$ is preferably in a range from about 0.1% to about 1% for typical corneal measurements. This range may change depending on the requirements of a specific application.

Figure 6A:
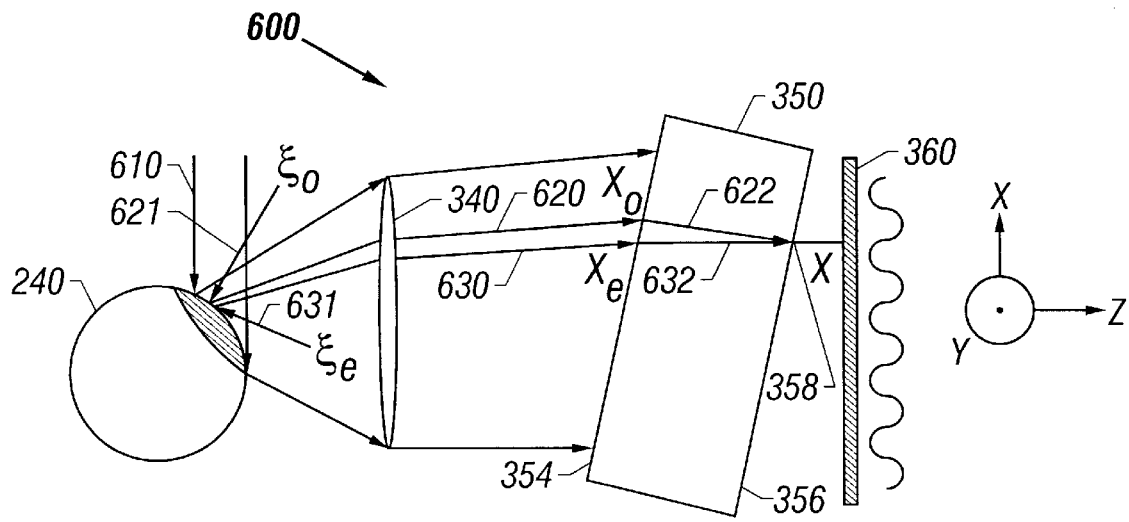
FIG. 6A is a schematic diagram showing a conoscopic geometry for extracting a corneal shape.

FIG. 6A illustrates an actual geometry 600 for extracting the three-dimensional corneal surface shape based on the conoscopic system 500. A collimated light beam 610 is incident upon the corneal surface of an eye 240 at an angle. The beam 610 is reflected to pass through a lens 340, a tilted uniaxial birefringent crystal 350, and a polarizer 360. Assume that the o-ray 622 of a ray 620 and the e-ray 632 of a ray 630 within the crystal 350 interfere with each other at a point 358 on the exit surface 356 and the rays 620 and 630 respectively originate at points 621 ($\xi_o$) and 631 ($\xi_e$) on the corneal surface of the eye 240. According to the present invention, the system controller 250 can be programmed to extract the corneal surface shape by processing the digitized fringe pattern based on the specific geometry of the conoscopic system.

Figure 6B:
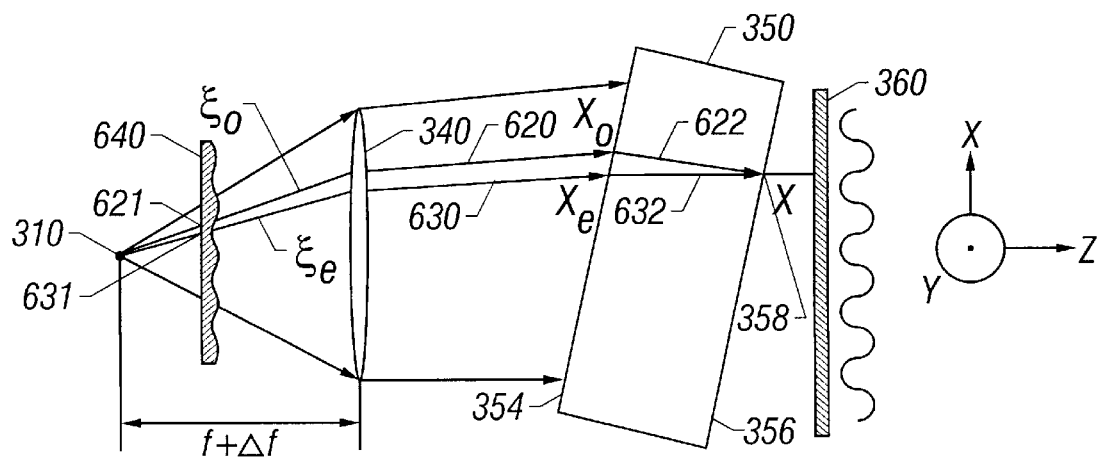
FIG. 6B is a simplified conoscopic geometry that is equivalent to the geometry of FIG. 6A.
Figure 7:
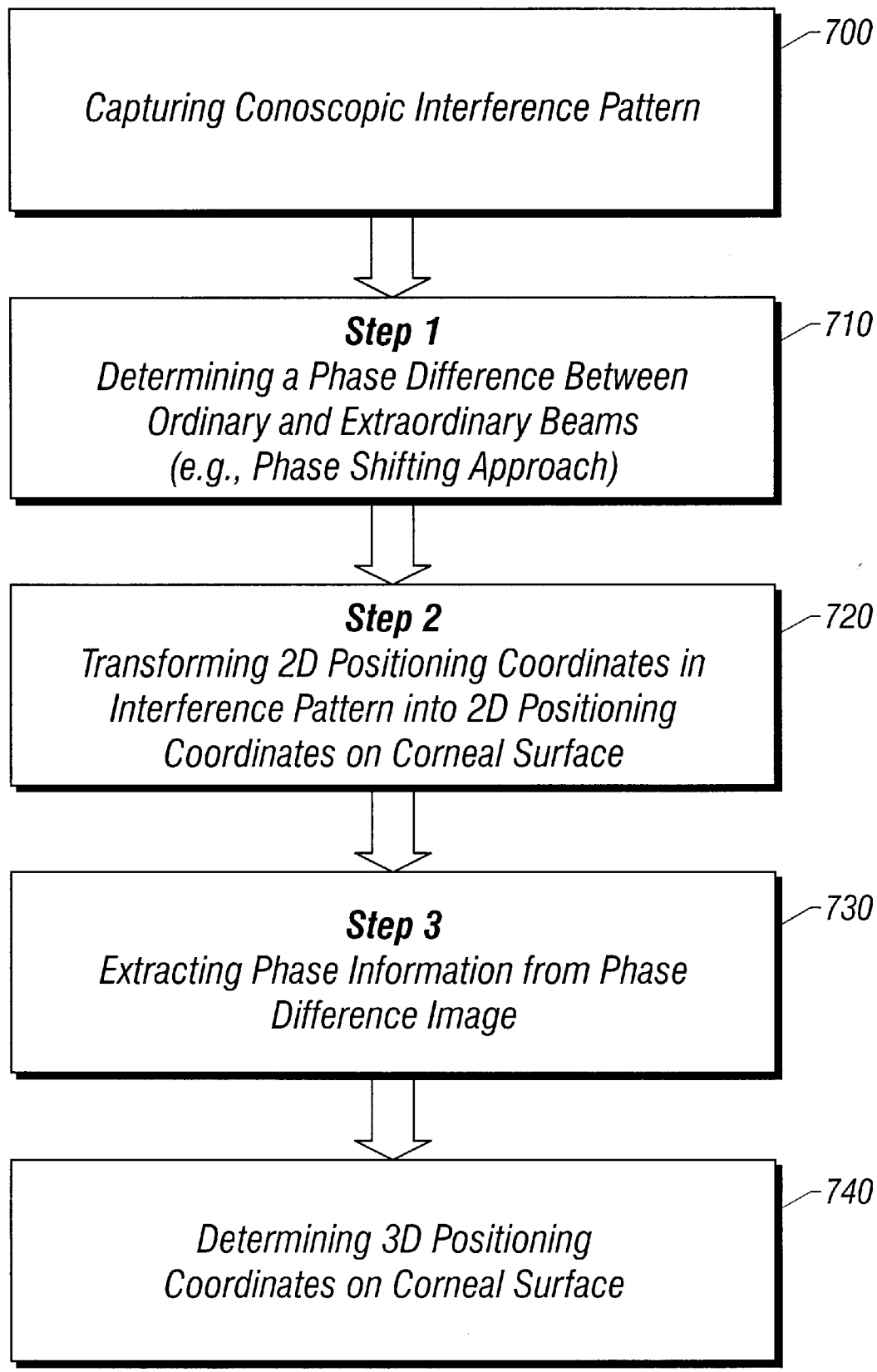
FIG. 7 is a flowchart of a shape extraction method based on conoscopic holography in accordance with the invention.

FIG. 6B shows a different geometry 601 that is equivalent to the actual geometry 600 in extracting the corneal shape. The equivalent geometry 601 is similar to the conoscopic geometry 300 of FIG. 3 with an addition of a transmissive phase aberrator 640. There are several differences between the actual geometry 600 and the equivalent geometry 601. In the actual geometry 600 for the corneal topography, the corneal surface to be measured is reflective rather than transmissive; the corneal surface is quasi-spherical rather than planar; the light is incident to the corneal surface at an angle rather than a normal incidence. However, there is an one-to-one correspondence between the systems 600 and 601 of FIGS. 6A and 6B, which is defined by a set of geometrical transformations. The geometry 601 is used to simplify the mathematical complexity of the extracting algorithm without losing physical traits of the actual geometry 600. For example, the phase distortion caused by the phase aberrator 640 is equivalent to the phase distortion of the corneal surface of the system 240 in the actual geometry 600. Therefore, it suffices to restrict the description of the extraction of the corneal shape to the simplified geometry 601 of FIG. 6B.

Referring to FIG. 6B, each ray emanating from the point source 310 attains a different phase-shift $\phi(\xi)$ depending on the point of intersection $\xi$ with the phase aberrator 640. The rays emitted by the point source 310 are collected by the lens 340 of a focal length f after passing through the phase aberrator 640. The point source 310 is located a distance, (f+$\Delta$f), away from the lens 340, therefore the light beam past the lens 340 has a degree of sphericity depending on the defocus $\Delta$f. As explained above, an interference pattern forms behind the polarizer 360 due to the phase difference between the e- and o-rays converging to the point 358 at the exit face 356 of the crystal 350. The two rays 620 and 630 intersect the aberrator surface at $\xi_e$ and $\xi_o$ respectively, which correspond to the two points 621 and 631 on the corneal surface of the eye 240 in FIG. 6A.

The conoscopic interference pattern I(x) obtained after the polarizer 360 can be approximately expressed in the following form:

$$I(x) = \frac{I_o}{2}\left[1 + \cos\left(\frac{2\pi G(x)}{\lambda}\right) + \phi(\xi_e) - \phi(\xi_o)\right], \quad (5)$$

where G(x) is given by Eq. (1). The extraction can be accomplished with the following three steps as shown in a flowchart 700 in FIG. 6.

In step 1 at 710, the phase difference $\phi(\xi_e)-\phi(\xi_o)$ is extracted by using a phase shifting method. Referring to FIG. 6B, the orientation of the birefringent crystal 350 about the y axis is changed to alter the optical path difference G(x) and thereby induces a phase shift in the interference pattern. Four different tilting angles of the crystal 350 are chosen in the following manner. An interference pattern I(0) is measured at an initial orientation of the crystal 350 at a tilt angle $\Psi_o$. The tilt angle $\Psi$ is then increased from $\Psi_o$ to a value $\Psi_1$ such that the phase shift in the interference pattern with respect to the initial title angle $\Psi_o$ is $\pi/2$. The measured interference pattern at $\Psi_1$ is represented by I($\pi/2$). The tilt angle $\Psi$ is subsequently increased to $\Psi_2$ and $\Psi_3$ to obtain interference patterns I($\pi$) and I($3\pi/2$), respectively. All measurements are performed for the same corneal surface. Based on the phase-shifted intensity patterns, the phase difference in Eq. (5) can be evaluated according the following equation:

$$\phi(\xi_e) - \phi(\xi_o) = \operatorname{atan}\left(\frac{I\left(\frac{3\pi}{2}\right) - I\left(\frac{\pi}{2}\right)}{I(0) - I(\pi)}\right). \quad (6)$$

The phase difference $\phi(\eta_e)-\phi(\eta_o)$ in an orthogonal direction ($\eta$) with respect to $\xi$ can be obtained in a similar manner.

The above phase shifting technique also allows a determination of the averaged intensity $I_0$ in Eq. (5). The intensity $I_0$ may be subtracted from the detected intensity pattern.

In step 2 at 720, a transformation between the coordinate x in the interference pattern captured by the imager 580 and the coordinates $\xi_e$ and $\xi_o$ on the phase aberrator 640 (equivalently, the coordinates in the x direction on the cornea) is performed. Thus, the positioning of the 2D interference pattern is transformed into 2D coordinates of the corneal surface in the xy-plane. A geometrical calculation shows that this relationship can be expressed with a quadratic formula, which may be stored in a look-up table. In a particular case where there is no defocus ($\Delta$f=0), the following linear approximation may be used for the transformation for small crystal tilt angle $\Psi$:

$$\frac{\xi_e + \xi_o}{2} = 2x - (\gamma_e + \gamma_o)L, \quad (7)$$

where $\gamma_e$ and $\gamma_o$ are given by the following equations:

$$\gamma_e = \frac{\sin\Psi}{\sqrt{n_e^2 - \sin^2\Psi}}, \quad (8)$$

$$\gamma_o = \frac{\sin\Psi}{\sqrt{n_o^2 - \sin^2\Psi}}. \quad (9)$$

In step 3 at 730, the spatial gradient of the phase difference, $\Delta\phi(\xi_e)-\Delta\phi(\xi_o)$, on the corneal surface is determined. The corneal surface variation along the z-direction can be determined. Therefore, the results of the steps 2 and 3 can be combined to extract three-dimensional surface shape. This is shown by a step 740 in FIG. 6.

According to the present invention, a preferred extraction technique uses a set of polynomials to represent the phase information of the corneal surface. For illustration purpose, mutually-orthogonal Hermite polynomials are used below as an example to the polynomial technique although other polynomials may also be used. Only one-dimensional analysis is described.

Hermite polynomials are conventionally defined as follows:

$$H_n(x) = (-1)^n e^{x^2} \frac{d^n}{dx^n} e^{x^2}. \quad (10)$$

It is known that any real function $\phi(x)$ with countable discontinuities can be uniquely expanded in terms of Hermite polynomials as follows:

$$\phi(x) = \sum_{j=0}^{\infty} b_j H_j(x). \quad (11)$$

In a typical practical application, the upper limit of the summation in Eq. (9) can be restricted to a selected finite integer J to achieve a sufficient accuracy. The specific number J is determined based on the requirements of an application and may vary from one application to another. If the function $\phi(x)$ contains components j>J, then integer J represents the accuracy of the polynomial expansion. Specifically, an upper summation limit of J=6 may be sufficient in many practical cases to obtain relatively smooth functions for mildly-deformed spherical surfaces such as the human cornea. Therefore, for a prespecified integer J, Eq. (9) can be approximated as:

$$\phi(x) \approx \sum_{j=0}^{J} b_j H_j(x). \tag{12}$$

The extraction of the corneal shape involves a difference function ω(x) of two functions of the same mathematical form with different variables as indicated by Eq. (5). The difference function ω(x) is recorded by the imager and is known. In term of the Hermite polynomials, ω(x) can be written as:

$$\begin{aligned}\omega(x) &= \phi(x+h) - \phi(x) \\ &\approx \sum_{j=0}^{J} b_j [H_j(x+h) - H_j(x)],\end{aligned} \tag{13}$$

where h represents the spatial separation of the ordinary and extraordinary rays at the exit surface 356 of the crystal 350 caused by the birefringence and $b_j$ are the expansion coefficients which are to be determined. If the expansion coefficients $b_j$ are known, the spatial gradient of the phase difference corresponding to the phase variation on the corneal surface is known. The surface shape can then be determined.

Alternatively, the difference function ω(x) may be approximately expressed in another expansion of the Hermite polynomials with a different set of coefficients $c_j$ up to (J−1) order:

$$\omega(x) = \phi(x+h) - \phi(x) \approx \sum_{j=0}^{J-1} c_j H_j(x). \tag{14}$$

Since ω(x) is known by measurements, the expansion coefficients $c_j$ can be readily derived by projecting ω(x) in the vector space $H_j(x)$ based on Eq. (12).

The shifted Hermite polynomials are known to have the following property:

$$H_n(x+h) - H_n(x) = \sum_{k=0}^{n-1} \frac{n!}{k!(n-k)!} (2h)^{n-k} H_j(x). \tag{15}$$

Using the above relation, the expansion coefficients, $b_j$, can be determined by using $c_j$. This is shown in the following Eqs. (14) and (15):

$$b_J = \frac{c_{J-1}}{2Jh}, \tag{16}$$

$$b_j = \frac{1}{2jh}\left[c_{j-1} - \sum_{k=j+1}^{J} \frac{k!}{(j-1)!(k-j+1)!} (2h)^{k-j+1} b_k \right]. \tag{17}$$

The coefficient $b_J$ is first determined by Eq. (14). Other $b_j$ can be subsequently determined with $c_j$ and $b_J$ by applying Eq. (15) for j decreasing from J down to 1. Each step requires only the coefficients calculated from the previous steps. Hence, the computational complexity is O(J). Note also that the coefficient $b_o$ is not included in Eqs. (14) and (15). This does not affect the measurement because $b_o$ is simply a constant bias and can be ignored.

One advantage of the Hermite polynomial expansion is that the difference pattern can be expressed analytically as shown by Eq. (13). This process is computationally simple and can be completed in a short computing cycle. This reduces computational cost. Another advantage is that it does not have singularity problems, which further simplifies the processing process.

Although the present invention has been described in detail with reference to a preferred embodiment, one ordinarily skilled in the art to which this invention pertains will appreciate that various modifications and enhancements may be predictable.

For example, the conoscopic topographer in accordance with the invention may be used for corneal shape measurements unrelated to PRK, such as the evaluation of radial keratectomy or thermo-laser keratoplasty. One of the advantages of using the conoscopic topographer is the better accuracy compared to conventional corneal topographers. The accuracy of a topographer according to the invention is on an order of one wavelength based on the fringe measurements. Other reflective surfaces that are substantially spherical may also be measured.

The spatial gradient of the phase difference between the ordinary and extraordinary waves may also be determined with other methods in addition to the Hermite polynomial technique. One alternative method calculates the spatial gradient at mid-points $\xi \approx (\xi_e + \xi_o)/2$, $\eta \approx (\eta_e + \eta_o)/2$ by the following approximation:

$$\frac{\partial \phi(\xi, \eta)}{\partial \xi} \approx \frac{\phi(\xi_e) - \phi(\xi_o)}{\xi_e - \xi_o}, \tag{18}$$

$$\frac{\partial \phi(\xi, \eta)}{\partial \eta} \approx \frac{\phi(\eta_e) - \phi(\eta_o)}{\eta_e - \eta_o}. \tag{19}$$

The actual height variation map of the corneal surface is extracted by a Taylor expansion approximation. The accuracy of this method is limited, especially at a location where the corneal surface has a steep variation in shape.

Another alternative method is based on fast Fourier transform ("FFT") of the conoscopic interference pattern. Assume Φ(u,v) is the Fourier transform of the unknown height map:

$$\Phi(u,v) = F[\phi(\xi, \eta)]. \tag{20}$$

The phase difference can be transformed as the following:

$$\begin{aligned}G_\xi(u, v) &\equiv F[\phi(\xi, \eta) - [\phi(\xi + h_\xi, \eta)] \\ &= (1 - e^{i2\pi u h_\xi})\Phi(u, v),\end{aligned} \tag{21}$$

$$\begin{aligned}G_\eta(u, v) &\equiv F[\phi(\xi, \eta) - [\phi(\xi, \eta + h_\eta)] \\ &= (1 - e^{i2\pi v h_\eta})\Phi(u, v).\end{aligned} \tag{22}$$

By inverting the above Fourier transforms, the original surface ϕ(ξ, η) is reconstructed with ambiguity only at spatial frequencies equal to multiples of $1/h_\xi$, $1/h_\eta$, that is, at the singularities of the shear kernel. Since mainly point-to-point operations or fast-Fourier transforms are involved in the FFT method, the operation may be performed at a high speed with dedicated electronics in the system controller 250. Allowing 20 msec for the phase extraction in the step 1 which is the most computationally expensive, the remaining two steps can be performed in less than 10 msec, thus meeting the real-time operation requirement.

These modifications and others are intended to be encompassed by the following claims.

What is claimed is:

1. A conoscopic topographer for obtaining topographic measurements of a substantially spherical target surface at a fixed position, comprising:

an illuminating device, producing a collimated probe beam to said target surface, said probe beam being of a probe wavelength to which said target surface is reflective;

a collecting lens disposed relative to said target surface at a predetermined distance, for receiving a reflected probe beam including said target surface, said reflected probe beam encoded with surface phase information indicative of said target surface;

an optical birefringent medium having a single optic axis, positioned relative to said collecting lens and oriented to form a tilted angle between a direction of said reflected probe beam and said optic axis, said birefringent medium splitting said reflected probe beam into an ordinary probe beam and an extraordinary probe beam which interfere with each other to form a conoscopic interference pattern;

a first polarizer, located in an optical path of said probe beam between said light source and said birefringent medium, operating to polarize said reflected probe beam in a first polarization direction;

an imager, receiving said conoscopic interference pattern and producing an electrical representation of said interference pattern; and a microprocessor, processing said electrical representation of said interference pattern to extract a topographic shape of said target surface.

2. A conoscopic topographer as in claim 1, wherein said illuminating device has a partially coherent light source.

3. A conoscopic topographer as in claim 1, wherein said illuminating device has an incoherent light source which has a pin hole at an output thereof.

4. A conoscopic topographer as in claim 1, wherein a ratio of an spectral linewidth of said probe beam to said probe wavelength is in a range from about 0.1% to about 1%.

5. A conoscopic topographer as in claim 1, wherein said collecting lens is so located relative to said target surface that a spacing between two adjacent fringes in said conoscopic interference pattern captured by said imager is maximized.

6. A conoscopic topographer as in claim 1, wherein said first polarization is selected relative to said optic axis of said birefringent medium so that said ordinary and extraordinary beams have a substantially identical power with respect to each other.

7. A conoscopic topographer as in claim 1, wherein said birefringent medium is a calcite crystal.

8. A conoscopic topographer as in claim 1, wherein said microprocessor extracts a direct phase information of said target surface from said interference pattern by using a Hermite polynomial expansion.

9. A photorefractive keratectomy surgical system, comprising:

a pulsed laser with a pulse repetition rate, producing an ablating laser beam at a wavelength at which a cornea is absorptive, said ablating laser beam having a fluence sufficient to ablate cornea tissue;

a beam steering system, located relative to said laser and guiding said ablating laser beam to a target eye which is at a fixed location;

a conoscopic topographer disposed relative to said fixed location, producing a probe beam to illuminate said target eye and receiving a reflected probe beam from said target eye, said topographer operable to measure a corneal shape of said target eye based on a conoscopic interference of said reflected probe beam; and a system controller having a microprocessor, electrically connected to said laser, said beam steering system, and said topographer, said controller controlling said topographer to achieve a corneal topographic measurement of said target eye at a processing rate higher than said pulse repetition rate.

10. A system as in claim 9, wherein said ablating laser beam is controlled by said controller based on said corneal topographic measurement of said target eye.

11. A system as in claim 10, wherein said control of said ablating laser beam affects said fluence.

12. A system as in claim 10, wherein said control of said ablating laser beam affects a beam impact position on said target eye.

13. A system as in claim 9, wherein said topographer comprises:

a light source, producing said probe beam;

a collimator, displaced relative to said light source, operating to collimate said probe beam;

a collecting lens disposed relative to said target eye at a predetermined distance for receiving said reflected probe beam whose wavefront is encoded with corneal surface phase information;

an optical birefringent crystal having a single optic axis, positioned relative to said collecting lens and orientated to form a tilted angle between a direction of said reflected probe beam and said optic axis, said crystal splitting said reflected probe beam into an ordinary probe beam and an extraordinary probe beam which interfere with each other to form a conoscopic interference pattern;

a first polarizer, located in an optical path of said probe beam between said light source and said crystal, operating to make said reflected probe beam polarize in a first polarization direction;

an imager, receiving said conoscopic interference pattern and producing an electrical representation of said interference pattern; and a second polarizer having a second polarization direction substantially orthogonal to said first polarization direction, located between said crystal and said imager, said second polarizer optimizing a detection of said imager.

14. A method for performing a topographic measurement of a spherical surface that is illuminated with a collimated probe beam, comprising:

imprinting a phase information of said spherical surface onto a reflected probe beam produced by said illumination of said probe beam;

generating a conoscopic interference pattern by using a uniaxial birefringent crystal to produce an ordinary beam and an extraordinary beam from said reflected probe beam;

determining a phase difference between said ordinary and extraordinary beams;

detecting a two-dimensional positioning representation of said spherical surface according to positioning coordinates in said conoscopic interference pattern;

extracting said phase information of said spherical surface based on said phase difference; and determining a three-dimensional representation of said spherical surface.

15. A method as in claim 14, wherein said phase difference is determined by performing a phase shifting process which comprises:

obtaining a first intensity distribution of said conoscopic interference pattern at a first orientation of said crystal to produce a first phase difference between said ordinary and extraordinary beams;

obtaining a second intensity distribution of said conoscopic interference pattern at a second orientation of said crystal to produce a second phase difference between said ordinary and extraordinary beams, said second orientation being chosen so that said second phase difference is shifted by about $\pi/2$ relative to said first phase difference;

obtaining a third intensity distribution of said conoscopic interference pattern at a third orientation of said crystal to produce a third phase difference between said ordinary and extraordinary beams, said third orientation being chosen so that said third phase difference is shifted by about n relative to said first phase difference; and obtaining a fourth intensity distribution of said conoscopic interference pattern at a fourth orientation of said crystal to produce a fourth phase difference between said ordinary and extraordinary beams, said fourth orientation being chosen so that said fourth phase difference is shifted by about $3\pi/2$ relative to said first phase difference.

16. A method as in claim 14, wherein said extracting of said phase information from said phase difference comprises:

representing said phase difference by a first polynomial expansion of Hermite polynomials to a first number of terms;

representing said phase difference by a second polynomial expansion of Hermite polynomials to a second number of terms, said second number being smaller than said first number by one;

determining a second set of expansion coefficients of said second polynomial expansion by projecting said phase difference in a vector space formed by said Hermite polynomials; and determining a first set of expansion coefficients of said first polynomial expansion based on said second set of expansion coefficients.

* * * * *